US011667655B2

(12) United States Patent
Arkles et al.

(10) Patent No.: US 11,667,655 B2
(45) Date of Patent: Jun. 6, 2023

(54) SILICON-BASED TETRAHYDROCANNABINOL DERIVATIVES AND COMPOSITIONS THEREOF

(71) Applicant: Gelest, Inc., Morrisville, PA (US)

(72) Inventors: Barry C. Arkles, Pipersville, PA (US); Taewoo Min, Langhorne, PA (US); Jonathan D. Goff, Philadelphia, PA (US)

(73) Assignee: GELEST, INC., Morrisville, PA (US)

( * ) Notice: Subject to any disclaimer, the term of this patent is extended or adjusted under 35 U.S.C. 154(b) by 292 days.

(21) Appl. No.: 17/117,682

(22) Filed: Dec. 10, 2020

(65) Prior Publication Data

US 2022/0185829 A1  Jun. 16, 2022

(51) Int. Cl.
C07F 7/08 (2006.01)
A61K 9/00 (2006.01)

(52) U.S. Cl.
CPC .......... *C07F 7/0838* (2013.01); *A61K 9/0014* (2013.01)

(58) Field of Classification Search
CPC .......................... C07F 7/0838; A61K 9/0014
USPC .......................................................... 514/63
See application file for complete search history.

(56) References Cited

FOREIGN PATENT DOCUMENTS

FR   2854896 A1   11/2004

OTHER PUBLICATIONS

Citti et al., "A novel phytocannabinoid isolated from *Cannabis sativa* L. with an in vivo cannabimimetic activity higher than Delta-9-tetrahydrocannabinol: Delta-9-tetrahydrocannabiphorol," Scientific Reports, vol. 9, No. 20335, pp. 1-13 (2019).
Damm et al., "An evaluation of microwave-assisted derivation procedures using hyphenated mass spectrometric techniques," Journal of Chromatography A, vol. 1216, No. 31, pp. 5875-5881 (2009) (Abstract Only).
Gunnar et al., "Validated toxicological determination of 30 drugs of abuse as optimized derivatives in oral fluid by long column fast gas chromatography/electron impact mass spectrometry," Journal of Mass Spectrometry, vol. 40, No. 6, pp. 739-753 (2005) (Abstract Only).
Harvey, D. J., "Allyldimethylsilyl ethers as derivatives for the characterization of steroids and cannabinoids by combined gas chromatography and mass spectrometry," Biomedical Mass Spectrometry, vol. 4, No. 4, pp. 265-274 (1977) (Abstract Only).
Harvey, D. J., "Cyclic alkylboronates as derivatives for the characterization of cannabinolic acids by combined gas chromatography and mass spectrometry," Biomedical Mass Spectrometry, vol. 4, No. 2, pp. 88-93 (1977) (Abstract Only).
Harvey, D. J., "The mass spectra of the trimethylsilyl derivatives of Delta-1- and Delta-6-tetrahydrocannabinol," Biomedical Mass Spectrometry, vol. 8, No. 12, pp. 575-578 (1981) (Abstract Only).
Harvey, D. J., "Vinyldimethylsilyl ethers as derivatives for the characterization of steroids and cannabinoids by gaschromatography mass spectrometry," Biomedical Mass Spectrometry, vol. 7, No. 5, pp. 211-216 (1980) (Abstract Only).
Harvey, D. J., "Vinyldimethylsilyl ethers, alkoxydialkylsilyl ethers and dimethoxymethylsilyl ethers: new derivatives for the characterization of steroids and cannabinoids by gas chromatography and mass spectrometry," Analytical Dhemistry Symposia Series, vol. 7 (Recent Dev. Mass Spectrom. Biochem., Med. Environ. Res.), pp. 315-325 (1981) (Abstract Only).
Karsak et al., "Attenuation of Allergic Contact Dermatitis Through the Endocannabinoid System," Science, vol. 316, pp. 1494-1497 (2007).
Knaus et al., "The separation, identification, and quantitation of cannabinoids and their t butyldimethylsilyl, trimethylsilylacetate, and diethylphosphate derivatives using high-pressure liquid chromatography, gas-liquid chromatography, and mass spectrometry," Journal of Chromatographic Science, vol. 14, No. 11, pp. 525-530 (1976) (Abstract Only).
Nadulski et al., "Simultaneous and sensitive analysis of THC, 11-OH-THC, THC-COOH, CBD, and CBN by GC-MS in plasma after oral application of small doses of THC and Cannabis extract," Journal of Analytical Toxicology, vol. 29, No. 8, pp. 782-789 (2005) (Abstract Only).
Pitt et al., "General synthesis of side-chain derivatives of cannabinoids," Journal of Organic Chemistry, vol. 44, No. 5, pp. 677-683 (1979) (Abstract Only).
Richardson et al., "Cannabinoids reduce hyperalgesia and inflammation via interaction with peripheral CB1 receptors," Pain, vol. 75, pp. 111-119 (1998).

(Continued)

*Primary Examiner* — Kristin A Vajda
(74) *Attorney, Agent, or Firm* — Panitch Schwarze Belisario & Nadel LLP

(57) ABSTRACT

Silicon-based tetrahydrocannabinol derivatives and methods for their synthesis are provided, in which the derivatives contain a tetrahydrocannabinol molecule and at least one silicon-based group containing Si—O—Si bonds. The derivatives are useful in topical and dermatological compositions, have potential beneficial topical properties, and enhance solubility and compatibility in topical and dermatological formulations containing the silicon-based materials.

18 Claims, No Drawings

(56) References Cited

OTHER PUBLICATIONS

Russo, Ethan B., "Cannabinoids in the management of difficult to treat pain," Therapeutics and Clinical Risk Management, vol. 4, No. 1, pp. 245-259 (2008).
Turner et al., "Constituents of *Cannabis sativa* L. XVIII. Electron voltage selected ion monitoring study of cannabinoids," Biomedical Mass Spectrometry, vol. 7, No. 6, pp. 247-256 (1980) (Abstract Only).
Nadulski et al., "Simple and sensitive determination of delta9-tetrahydrocannabinol, cannabidiol and cannabinol in hair by combined silylation, headspace solid phase microextraction and gas chromatography-mass spectrometry," Journal of Chromatography B, vol. 846, pp. 78-85 (2007).
International Search Report and Written Opinion dated Jul. 30, 2021 in International Application No. PCT/US2020/064235.

SILICON-BASED TETRAHYDROCANNABINOL DERIVATIVES AND COMPOSITIONS THEREOF

BACKGROUND OF THE INVENTION

Tetrahydrocannabinol (THC) is a phytocannabinoid which is known to have anti-inflammatory activity. It is the primary psychoactive cannabinoid and is known to bind to cannabinoid receptors (CB1 and CB2) to reduce pain, inflammation, and hyperalgesia (see, for example, Citti et al, *Sci. Rep.* 9, 20335 (2019); Karsak et al, *Science,* 316, 1494 (2007); Richardson et al, *Pain,* 75, 111 (1998)). Tetrahydrocannabinol is the designated name for (6aR,10aR)-6,6,9-trimethyl-3-pentyl-6a,7,8,10a-tetrahydro-6H-benzo[c]chromen-1-ol, shown below:

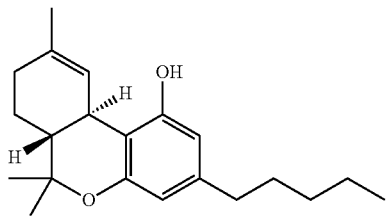

(I)

Topical formulations of tetrahydrocannabinol have been reported to reduce allergic inflammation (Karsak et al, *Science,* 316, 1494-1497 (2007)). Pure tetrahydrocannabinol has low stability in air, light, acid media, and at high temperature, but derivatives of tetrahydrocannabinol with increased in stability would be attractive. Also desirable would be derivatives having lower surface tension, which would enable the formation of thin films either directly or by enhancing solubility in low surface tension fluids, such as silicones.

BRIEF SUMMARY OF THE INVENTION

A silicon-based tetrahydrocannabinol derivative according to an embodiment of the disclosure contains a silicon-based functional group containing Si—O—Si bonds which is bound to a tetrahydrocannabinol molecule having Formula (I):

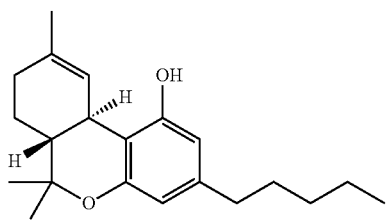

(I)

A topical or dermatological formulation according to an embodiment of the disclosure contains a base formulation and at least one silicon-based tetrahydrocannabinol derivative comprising at least one silicon-based functional group containing Si—O—Si bonds which is bound to a tetrahydrocannabinol molecule having Formula (I):

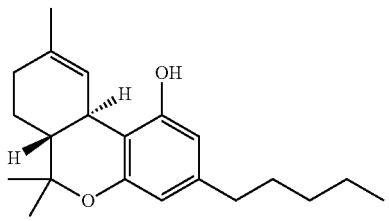

(I)

DETAILED DESCRIPTION OF THE INVENTION

The disclosure relates to compositions containing derivatives of tetrahydrocannabinol (THC) containing a silicon-containing functional group which are beneficial for various applications, including the formulation of topical medicinal products and personal care products, and methods for their preparation. The silicon-containing tetrahydrocannabinol derivatives described herein are unique hybrid organosilicon compounds formed by attaching tetrahydrocannabinol to a siloxane backbone, also described as a molecule comprising one silicon-based functional group containing Si—O—Si bonds which is bound to a tetrahydrocannabinol molecule. Although the binding affinity for cannabinoid acceptors of the compounds described herein has not yet been studied, they are expected to provide increased stability and solubility and to release the free tetrahydrocannabinol uniformly and over a prolonged period.

As used herein, the terms tetrahydrocannabinol and THC are intended to encompass all isomers of tetrahydrocannabinol, including those found naturally or developed synthetically.

Preferred embodiments of the compounds of the disclosure include trisiloxanyl derivatives of tetrahydrocannabinol in which a siloxane-based group is bound through the phenolic hydroxyl group of the tetrahydrocannabinol molecule, forming an Si—O—C bond.

The silicon-based tetrahydrocannabinol derivatives include a tetrahydrocannabinol molecule, such as shown in Formula (I), having a silicon-based group as a functional group. Most preferably, the silicon-based group is a siloxanyl group or a trialkoxysilane-containing group.

Preferred tetrahydrocannabinol derivatives described herein have a structure in accordance with Formula (I) above in which the phenolic hydroxyl group is bound to a siloxane moiety containing two or more silicon atoms, preferably three or more silicon atoms, most preferably about 3 to about 10 silicon atoms.

Tetrahydrocannabinol derivatives according to embodiments of the invention have general formula (A). In this formula, R may be, for example and without limitation, $SiMe(OSiMe_3)_2$, $SiMe_2(OSiMe_2)_4CH_2CH_2CH_2CH_3$, $SiMe_2OSiMe_3$, and $SiMe_2OSiMe_2C_6H_5$, in which "Me" is a methyl group. However, compounds having formula (A) that are within the scope of the disclosure are not limited to these substituents, and other silicon-containing functional groups having Si—O—Si bonds that are known in the art or to be developed would also be suitable for R.

Substituents containing a single silicon atom without an oxane (oxygen) bridge between two or more silicon atoms are not within the scope of the disclosure because such tetrahydrocannabinol derivatives fail to provide acceptable film-forming properties. For example, simple trialkylsilyl derivatives, as well as derivatives containing only alkyl, aryl, hydrogen, halogen, vinyl, allyl and/or alkoxy substituents on the silicon are not within the scope of the disclosure as these are not effective for the intended purpose.

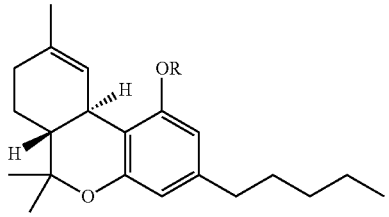

(A)

Other compounds within the scope of the disclosure include polydimethylsiloxanes in which the tetrahydrocannabinol substitutes through the phenolic oxygen in place of a methyl group on a polydimethylsiloxane, such as $Me_3Si(OSiMe_2)_m(OSiMeTHC)_nSiMe_3$, in which "THC" represents tetrahydrocannabinol, Me is a methyl group, and m and n are integers. Preferably, m is 1 to about 100 and n is 1 to about 10.

The silicon-based tetrahydrocannabinol derivatives according to embodiments of the disclosure include a wide variety of derivatized compounds, including most preferred compounds such as, for example, (tetrahydrocannabinoloxy)heptamethyltrisiloxane (formula (II)), tetrahydrocannabinoloxy-terminated polydimethylsiloxane (formula (III)), and tetrahydrocannabinoloxypropyl-terminated polydimethylsiloxane (formula (IV)), shown below, in which m and n are integers; preferably m is 1 to about 100 and n is 1 to about 10.

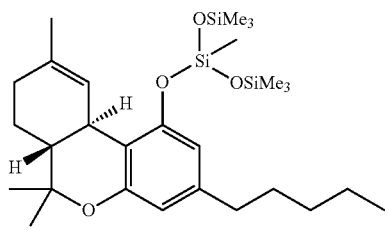

(II)

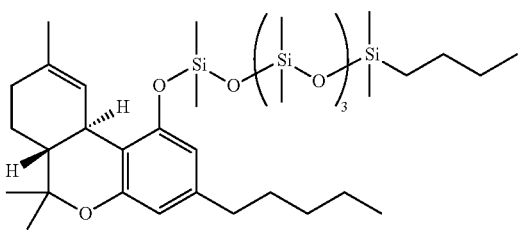

(III)

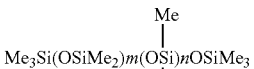

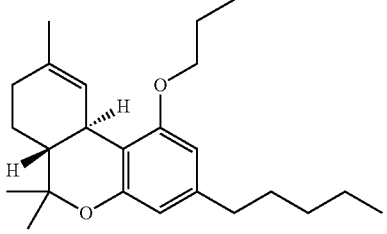

(IV)

Compounds according to embodiments of the disclosure may contain a direct ether linkage between the silicon-containing functional group and the phenolic hydroxyl group of the tetrahydrocannabinol molecule (direct Si—O bond) or may contain an alkyl group spacer between the phenolic hydroxyl group on tetrahydrocannabinol and the silicon-based functional group, such as compounds in which R in formula (A) is $CH_2SiMe_2OSiMe_3$ or $CH_2SiMe_2OSiMe_2C_6H_5$. The spacer is not limited to $CH_2$, and may also be a longer alkyl chain containing up to about 11 carbon atoms, such as $(CH_2)_3$, which, along with $CH_2$, is also a preferred embodiment.

Compounds according to embodiments of the disclosure which contain an alkyl group spacer between the phenolic hydroxyl group on tetrahydrocannabinol and the silicon-based functional group may have general formula (B) below, in which R' is a silicon-based group and x is an integer ranging from 1 to about 11, preferably 1 (methyl) to 3 (propyl). Most preferably, the silicon-based group is a siloxanyl group or a trialkoxysilane-containing group. R' may be, for example and without limitation, $SiMe(OSiMe_3)_2$, $SiMe_2(OSiMe_2)_4CH_2CH_2CH_2CH_3$, $SiMe_2OSiMe_3$, or $SiMe_2OSiMe_2C_6H_5$, in which Me is methyl.

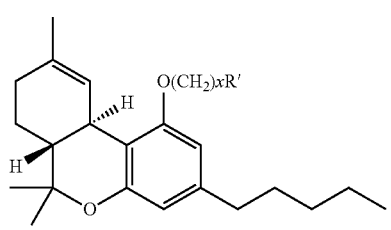

(B)

Direct Si—O linkage of the tetrahydrocannabinol derivatives, such as shown in formula (A), may result in diminished allergic inflammation by releasing free tetrahydrocannabinol over a prolonged period by slow hydrolysis. The Si—O bond on tetrahydrocannabinol derivatives is not stable when exposed to moisture, which results in slow decomposition of compounds to form free tetrahydrocannabinol and low molecular weight siloxanes. The silane-based tetrahydrocannabinol derivatives are anticipated to be stable when stored in air and protected from moisture. They are anticipated to show bioactivity in medicinal applications either directly or by slow hydrolysis to form underivatized THC.

Unlike many silicones and silicone derivatives, these compounds are easily incorporated into topical or dermatological products, including anti-inflammatory and palliative formulations, due to their solubility in a range of polar compounds such as castor oil and a variety of cosmetic or dermatological vehicles. They may also act as co-solvents for silicones. Further, due to such solubility, these derivatives may be useful as compatibilizers for other bioactives, such as unmodified cannabidiol and tetrahydrocannabinol compounds, among other possible applications.

The tetrahydrocannabinol derivatives described herein may be prepared by various synthetic pathways. In accordance with one embodiment of the disclosure, the compounds may be prepared by reacting the hydroxyl group on the benzenoid ring of tetrahydrocannabinol with an allylic halide in a solvent to form an allyloxytetrahydrocannabinol intermediate, and then hydrosilylating the intermediate with a silane compound and catalyst to form a silicon-based tetrahydrocannabinol derivative with a spacer. It is also within the scope of this disclosure to form a direct Si—O linkage on the hydroxyl group of tetrahydrocannabinol by reacting the hydroxyl group (C—OH) with a chlorine-containing siloxane compound (—Si—Cl) in the presence of a base acceptor, or by the dehydrogenative coupling of the hydroxyl group with a hydride-containing siloxane compound (—Si—H). Another possible synthetic route to form the direct Si—O linkage is the formation of an alkali metal alkoxide intermediate (—C—O—Na) and reacting the intermediate with either a Si—Cl or Si—H containing siloxane compound. Reaction to form a hydrocarbon bridge proceeds by the addition of a hydride containing siloxane (—Si—H) across a C═C double bond by a hydrosilylation reaction.

The silane compounds used in the reactions described above may be any of a wide variety of silicon-based compounds, and preferably include alkylsilanes, alkoxysilanes, alkylsiloxanes and alkoxysiloxanes and their derivatized or functionalized counterparts. In general, it is preferred to have two or more silicon atoms in the substitution in order to provide solubility and spreading characteristics suitable for topical creams and ointments. Examples include, without limitation, bis(trimethylsiloxy)methylsilane, bis(trimethylsiloxy)ethylsilane, bis(trimethylsiloxy)propylsilane, bis(triethylsiloxy)methylsilane, bis(triethylsiloxy)ethylsilane, bis(triethylsiloxy)propylsilane, triethoxysilane, trimethoxysilane, tripropylsilane, bis(tripropylsiloxy)methylsilane, bis(tripropylsiloxy)ethylsilane, bis(tripropylsiloxy)propylsilane and similar compounds.

Also useful as silane compounds herein are polymeric silicon-containing molecules having similar reactive capabilities as the silane monomeric structures noted above, such as polydimethylsiloxane, polydiethylsiloxane, polydipropylsiloxane, polymethylethylsilane, polymethylpropylsiloxane, and other polyalkyl- or polyalkenyl-siloxanes as are known in the art or to be developed. Chain lengths may vary, but it is preferred that the molecular weight (Mn) of polymeric silane compounds used to form polymeric silicon-based derivative groups on tetrahydrocannabinol be from 100 to about 5000, and most preferably from about 500 to about 2000. It should be noted that variations in molecular weight above and below this range are within the scope of the disclosure and that the components having different chain lengths may contribute varying properties accordingly. For example, generally, lower molecular weight chains would tend to be more emollient in nature, while higher molecular weight chains would tend to be more substantive in terms of being longer-wearing on skin and more resistant to wash-off.

It should also be understood that the derivatives described herein may be produced using pure tetrahydrocannabinol. Alternatively, the derivatives may be formed and provided as a component of phytocannabinoid and/or other phytochemical mixtures. For example, the tetrahydrocannabinol derivative of cannabis extracts may be formed without isolating the pure tetrahydrocannabinol component. Further, compositions according to the invention may contain one or more of the derivatives described herein and one or more phytochemicals extracted from cannabis.

The silicon-based tetrahydrocannabinols described herein may be used in various topical and dermatological compositions, including preferably those which have silicon compounds or silicone-based polymers in the base formulation because the derivatives facilitate compatibility and solubility in such compounds within formulations. However, the disclosure is not limited to those compositions and may include any topical or dermatological composition in which the silicon-based tetrahydrocannabinol derivatives are useful. The cosmetic and topical compositions of the present disclosure include a base formulation, which may be any suitable topical or dermatological base formulation as described above, and at least one silicon-based tetrahydrocannabinol derivative as described herein. The silicon-based tetrahydrocannabinol derivatives include a tetrahydrocannabinol molecule or a commercial or natural derivative thereof and include a silicon-based functional group bonded to the tetrahydrocannabinol molecule (or the derivative thereof) through the oxygen atom of the benzenoid ring.

When incorporated in such formulations, it is preferred that the silicon-based tetrahydrocannabinol derivative is present in an amount of about 0.01 percent by weight to about 20 percent by weight, preferably about 0.5 percent by weight to about 5 weight percent and most preferably about 0.5 to about 1.0 percent by weight based on the weight of the formulation.

The invention will now be described in connection with the following, non-limiting examples.

Example 1: Synthesis of 1,1,1,3,5,5,5-heptamethyl-3-(((6aR,10aR)-6,6,9-trimethyl-3-pentyl-6a,7,8,10a-tetrahydro-6H-benzo[c]chromen-1-yl)oxy)trisiloxane (II)

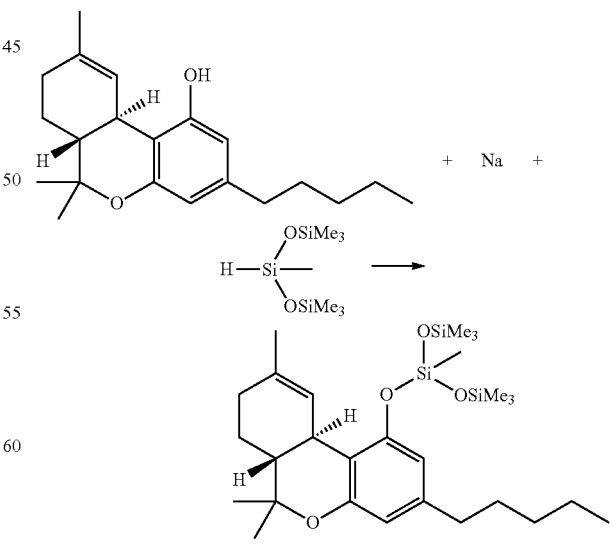

(II)

Sodium (0.55 g, 0.02 mol) and tetrahydrofuran (13.42 g) are charged to a reactor. A solution of tetrahydrocannabinol (6.29 g, 0.02 mol) in tetrahydrofuran (37.98 g) is added dropwise over 30 min while keeping pot temperature below 70° C. The resulting reaction mixture is stirred at 50-60° C. until all sodium has been consumed. Bis(trimethylsiloxy) methylsilane (6.77 g, 0.03 mol) is added dropwise over 10 min at 70° C., then the reaction mixture is heated at 110-120° C. for 10 h. The reaction mixture is filtered through silica gel (40 g) and washed with tetrahydrofuran (400 g). The filtrate is concentrated in vacuo. The residue contains the product and unreacted tetrahydrocannabinol and is analyzed by $^1$H NMR and FTIR.

Example 2: Synthesis of 1-butyl-1,1,3,3,5,5,7,7,9,9-decamethyl-9-(((6aR,10aR)-6,6,9-trimethyl-3-pentyl-6a,7,8,10a-tetrahydro-6H-benzo[c]chromen-1-yl)oxy)pentasiloxane (III)

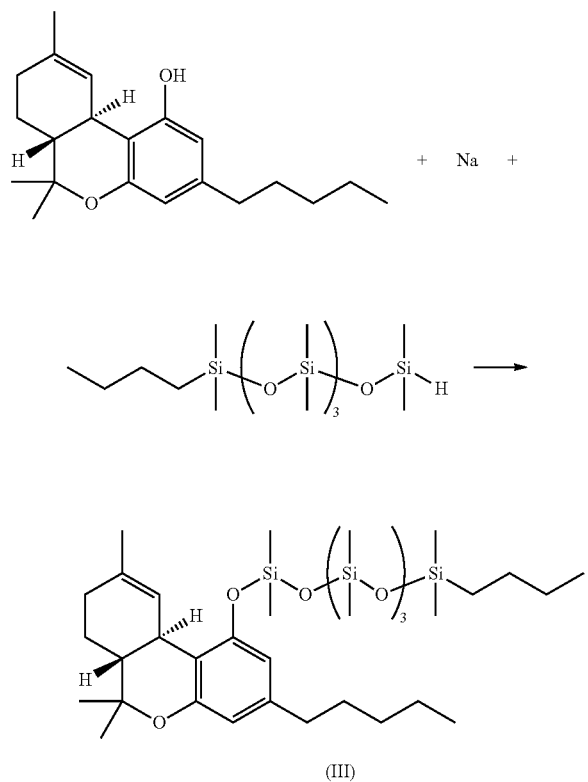

(III)

Sodium (0.55 g, 0.02 mol) and tetrahydrofuran (13.42 g) are charged to a reactor. A solution of tetrahydrocannabinol (6.29 g, 0.02 mol) in tetrahydrofuran (37.98 g) is added dropwise over 30 min while keeping pot temperature below 70° C. The resulting reaction mixture is stirred at 50-60° C. until all sodium has been consumed. 1-Butyl-1,1,3,3,5,5,7,7,9,9-decamethylpentasiloxane (12.39 g, 0.03 mol) is added dropwise over 10 min at 70° C., then the reaction mixture is heated at 110-120° C. for 10 h. The reaction mixture is filtered through silica gel (40 g) and washed with tetrahydrofuran (400 g). The filtrate is concentrated in vacuo. The residue contains the product and unreacted tetrahydrocannabinol and is analyzed by $^1$H NMR and FTIR.

Example 3: Tetrahydrocannabinoloxypropyl-terminated polydimethylsiloxane (IV)

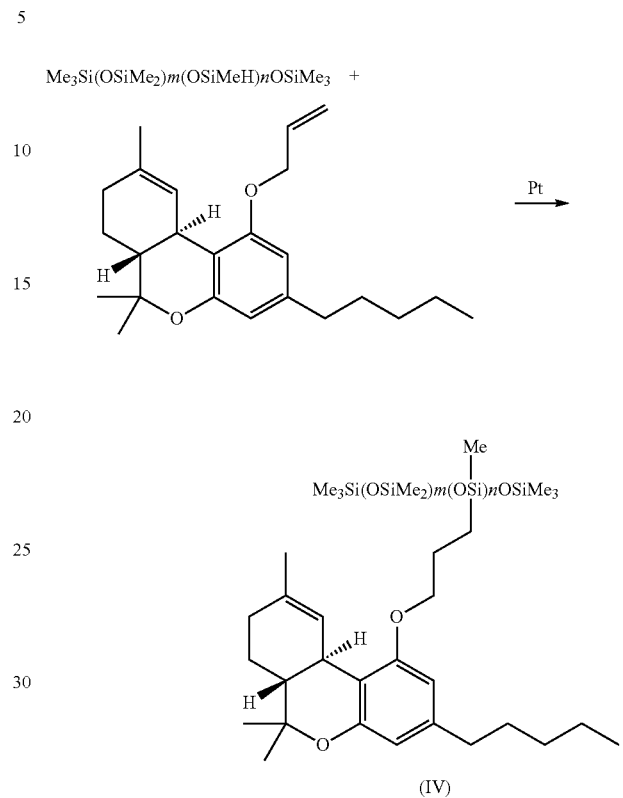

(IV)

Allyloxytetrahydrocannabinol (70.9 g, 0.2 mol) and toluene (50mL) are charged to a reactor. The resulting mixture is heated to 80-90° C. Karstedt catalyst (2% Pt concentration in xylene, 0.5 mL) is added when pot temperature reaches 80-90° C. Hydride-terminated polydimethylsiloxane (Mn-1050, 105 g) is added dropwise while controlling the exotherm, then the reaction mixture is heated at 85-115° C. until FTIR indicates that all Si—H has been consumed. Activated charcoal is added to the mixture and stirred overnight. The mixture is filtered and the filtrate is concentrated in vacuo. The residue contains the product and unreacted tetrahydrocannabinol and is analyzed by $^1$H NMR and FTIR.

It will be appreciated by those skilled in the art that changes could be made to the embodiment described above without departing from the broad inventive concepts thereof. Also, based on this disclosure, a person of ordinary skill in the art would further recognize that the relative proportions of the components illustrated above could be varied without departing from the spirit and scope of the invention. It is understood, therefore, that this invention is not limited to that particular embodiment disclosed, but it is intended to cover modifications within the spirit and scope of the present invention as defined by the appended claims.

We claim:

1. A silicon-based tetrahydrocannabinol derivative comprising a silicon-based functional group containing Si—O—Si bonds which is bound to a tetrahydrocannabinol molecule having formula (I):

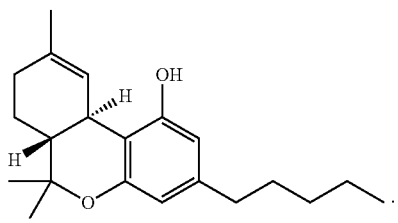

(I)

2. The silicon-based tetrahydrocannabinol derivative according to claim 1, wherein the silicon-based functional group is bound to the tetrahydrocannabinol molecule by a phenolic oxygen atom in the benzenoid ring.

3. The silicon-based tetrahydrocannabinol derivative according to claim 1, wherein the silicon-based functional group is a siloxanyl group or a trialkoxysilane-containing group.

4. The silicon-based tetrahydrocannabinol derivative according to claim 1, wherein the silicon-based functional group contains at least two silicon atoms.

5. The silicon-based tetrahydrocannabinol derivative according to claim 1, having formula (A), wherein R is SiMe(OSiMe$_3$)$_2$, SiMe$_2$(OSiMe$_2$)$_4$CH$_2$CH$_2$CH$_2$CH$_3$, SiMe$_2$OSiMe$_3$, SiMe$_2$OSiMe$_2$C$_6$H$_5$, CH$_2$SiMe$_2$OSiMe$_3$ or CH$_2$SiMe$_2$OSiMe$_2$C$_6$H$_5$, and wherein Me represents a methyl group:

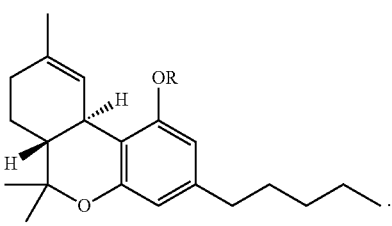

(A)

6. The silicon-based tetrahydrocannabinol derivative according to claim 1, having formula (B), wherein R' is SiMe(OSiMe$_3$)$_2$, SiMe$_2$(OSiMe$_2$)$_4$CH$_2$CH$_2$CH$_2$CH$_3$, SiMe$_2$OSiMe$_3$, or SiMe$_2$OSiMe$_2$C$_6$H$_5$, Me represents a methyl group, and x is an integer ranging from 1 to about 11:

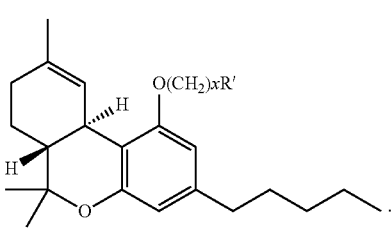

(B)

7. The silicon-based tetrahydrocannabinol derivative according to claim 1, having formula (II), wherein Me represents a methyl group:

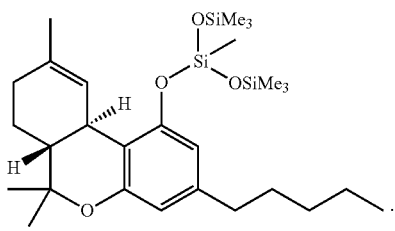

(II)

8. The silicon-based tetrahydrocannabinol derivative according to claim 1, having formula (III):

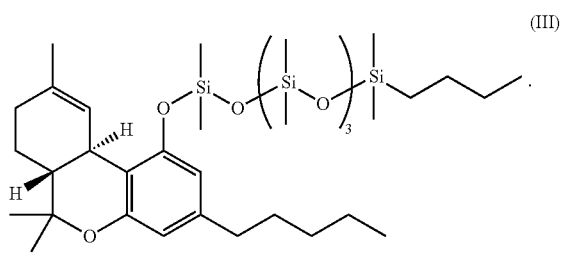

(III)

9. The silicon-based tetrahydrocannabinol derivative according to claim 1, having formula (IV), wherein Me represents a methyl group, m is an integer from 1 to about 100, and n is an integer from 1 to about 10:

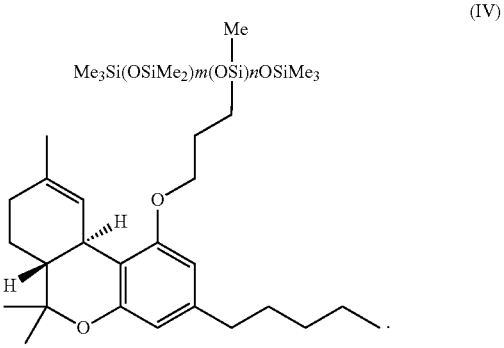

(IV)

10. A topical or dermatological composition comprising a base formulation and at least one silicon-based tetrahydrocannabinol derivative, wherein the at least one silicon-based tetrahydrocannabinol derivative comprises a silicon-based functional group containing Si—O—Si bonds which is bound to a tetrahydrocannabinol molecule having formula (I):

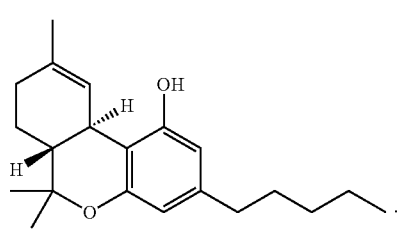

(I)

11. The topical or dermatological composition according to claim 10, wherein the silicon-based functional group is bound to the tetrahydrocannabinol molecule by a phenolic oxygen atom in the benzenoid ring.

12. The topical or dermatological composition according to claim 10, wherein the silicon-based functional group is a siloxanyl group or a trialkoxysilane-containing group.

13. The topical or dermatological composition according to claim 10, wherein the silicon-based functional group contains at least two silicon atoms.

14. A method for making the silicon-based tetrahydrocannabinol derivative according to claim 1, comprising reacting tetrahydrocannabinol with an allylic halide in a solvent to form an allyloxytetrahydrocannabinol intermediate, and reacting the allyloxytetrahydrocannabinol intermediate with a silane compound and a catalyst to form the silicon-based tetrahydrocannabinol derivative.

15. A method for making the silicon-based tetrahydrocannabinol derivative according to claim 1, comprising forming a silylated alkyl ether on a tetrahydrocannabinol molecule by reacting a chlorine-containing siloxane compound with a hydroxyl group in the presence of a base acceptor.

16. A method for making the silicon-based tetrahydrocannabinol derivative according to claim 1, comprising forming a silylated alkyl ether on a tetrahydrocannabinol molecule by dehydrogenative coupling of a hydride-containing siloxane.

17. A method for making the silicon-based tetrahydrocannabinol derivative according to claim 1, comprising forming a silylated alkyl ether on a tetrahydrocannabinol molecule by forming an intermediate alkali metal alkoxide followed by reaction with a silicon-hydride or silicon-chlorine containing compound.

18. A composition comprising the silicon-based tetrahydrocannabinol derivative according to claim 1 and at least one phytochemical extracted from cannabis.

* * * * *